(12) United States Patent
Weinschenk, III

(10) Patent No.: US 10,029,229 B2
(45) Date of Patent: Jul. 24, 2018

(54) ADJUSTABLE CHROMOPHORE COMPOUNDS AND MATERIALS INCORPORATING SUCH COMPOUNDS

(71) Applicant: Novartis AG, Basel (CH)

(72) Inventor: Joseph I. Weinschenk, III, Fort Worth, TX (US)

(73) Assignee: Novartis AG, Basel (CH)

( * ) Notice: Subject to any disclaimer, the term of this patent is extended or adjusted under 35 U.S.C. 154(b) by 203 days.

(21) Appl. No.: 14/792,877

(22) Filed: Jul. 7, 2015

(65) Prior Publication Data

US 2015/0306562 A1    Oct. 29, 2015

Related U.S. Application Data

(62) Division of application No. 13/076,665, filed on Mar. 31, 2011, now abandoned.

(60) Provisional application No. 61/320,442, filed on Apr. 2, 2010.

(51) Int. Cl.

| *B01J 19/10* | (2006.01) |
| *A61L 27/50* | (2006.01) |
| *B29D 11/00* | (2006.01) |
| *C07D 249/20* | (2006.01) |
| *C08K 5/34* | (2006.01) |
| *G02B 1/04* | (2006.01) |
| *B01J 19/12* | (2006.01) |
| *C08K 5/3475* | (2006.01) |

(52) U.S. Cl.
CPC ............ *B01J 19/123* (2013.01); *A61L 27/50* (2013.01); *B01J 19/127* (2013.01); *B29D 11/00461* (2013.01); *C07D 249/20* (2013.01); *C08K 5/3475* (2013.01); *G02B 1/043* (2013.01); *A61L 2430/16* (2013.01)

(58) Field of Classification Search
CPC .... A61L 27/50; A61L 2430/16; B01J 19/123; B01J 19/127; B29D 11/00461; C07D 249/20; C08K 5/3475; G02B 1/043
See application file for complete search history.

(56) References Cited

U.S. PATENT DOCUMENTS

| 4,528,311 | A  | 7/1985  | Beard et al. |
| 6,864,325 | B2 | 3/2005  | Zedda et al. |
| 7,396,942 | B2 | 7/2008  | Schuleter |
| 7,459,106 | B2 | 12/2008 | Marder et al. |
| 2002/0025401 | A1 | 2/2002 | Berg et al. |
| 2004/0186241 | A1* | 9/2004 | Gemert ................. A61F 2/1659 |
| | | | 525/329.7 |
| 2007/0077214 | A1 | 4/2007 | Laszlo et al. |
| 2007/0286969 | A1* | 12/2007 | Nagpal ............. C08G 18/3237 |
| | | | 428/1.31 |
| 2008/0090937 | A1 | 4/2008 | Jinkerson et al. |
| 2008/0242818 | A1 | 10/2008 | Benz et al. |
| 2009/0157178 | A1 | 6/2009 | Hampp |
| 2010/0012889 | A1 | 1/2010 | Jinkerson |

FOREIGN PATENT DOCUMENTS

| CN | 1317535 A | 10/2001 |
| JP | 49-61142 A | 6/2012 |
| RU | 2008101450 A | 7/2009 |
| WO | 2007140058 | 12/2007 |
| WO | 2008048880 | 4/2008 |

OTHER PUBLICATIONS

PCT International Search Report for corresponding PCT/US2011/030634 dated Jul. 13, 2011.
PCT Written Opinion for corresponding PCT/US2011/030634 dated Jul. 13, 2011.

* cited by examiner

*Primary Examiner* — Amina S Khan
(74) *Attorney, Agent, or Firm* — Patrick M. Ryan

(57) ABSTRACT

The present invention is directed to adjustable chromophore compounds and materials (e.g., ophthalmic lens materials) incorporating those compounds. The adjustable chromophore compounds include a chemical moiety that structurally changes upon exposure to predetermined electromagnetic radiation (e.g., two photon radiation) as well as lens materials, particularly intraocular lens materials that incorporate those compounds.

4 Claims, 1 Drawing Sheet

ADJUSTABLE CHROMOPHORE COMPOUNDS AND MATERIALS INCORPORATING SUCH COMPOUNDS

CROSS REFERENCE TO RELATED APPLICATION

This application is a divisional of U.S. Utility patent application Ser. No. 13/076,665 filed Mar. 31, 2011, now abandoned, which claims priority under 35 U.S.C. § 119 to U.S. Provisional Patent Application Ser. No. 61/320,442, filed Apr. 2, 2010, the entire contents of which are incorporated herein by reference.

TECHNICAL FIELD OF THE INVENTION

The present invention is related to adjustable chromophore compounds and materials (e.g., ophthalmic lens materials) incorporating those compounds. More particularly, the present invention is related to adjustable chromophore compounds that includes a chemical moiety that structurally changes upon exposure to predetermined electromagnetic radiation (e.g., two photon radiation) as well as lens materials (e.g., intraocular lens materials) that incorporate those compounds.

BACKGROUND OF THE INVENTION

Chromophore compounds are molecules that absorb light and such light absorption is desirable for a wide range of products. They are particularly important and useful in lenses of many different types. As examples, chromophores have been incorporated into lenses of sunglasses, lenses of spectacles, contact lenses and intraocular lenses (IOLs). As such, a significant amount of research has been performed investigating a wide variety of compounds with light absorption characteristics.

It is typical for lenses such as those mentioned above to be formed of polymeric or glass matrices. Advantageously, the chromophores can be dispersed or distributed throughout portions or the entirety of the matrices and the concentrations of the chromophores can be substantially homogeneous throughout the matrices or the concentrations can be varied in certain portions of the matrices.

For lenses, the amount and type (e.g., wavelength) of light absorption provided by any particular chromophore typically depends upon the amount and type (e.g., chemical structure) of chromophore used in a particular lens. This type and amount of chromophore is typically predetermined and provides the lens with a particular predetermined light absorption profile. While this is generally acceptable for most lenses, there are circumstances in which it may be desirable to change the absorption characteristics of a chromophore after it has been incorporated into a lens thereby changing the absorption profile provided by the lens itself.

As one example, individuals having intraocular lens (IOLs) may be particularly desirous of having the ability to change the absorption profile provided by the chromophores in their lenses. Individuals that will be exposed to greater amounts of sunlight due to geographical changes, activity (e.g., employment) changes or other changes in their lives may desire a change in the absorption profile of their IOLs. Individuals that have or develop sensitivity to particular wavelengths of light may desire a change in the absorption profile. It would also be desirable to be able to tune the absorption profile of an IOL for all individuals receiving IOLs.

It is also the case that some chromophore compounds tend to degrade over time due to absorption of light. In this circumstance, it would be desirable to be able to adjust the absorption profile of the lens to compensate for the degradation of the chromophores.

In view of the above, it would be particularly desirable to provide a chromophore with adjustable light absorption characteristics. It would also be particularly desirable to provide such chromophore compound within a product (e.g., lens) wherein the absorption profile of the lens could be adjusted after incorporation of the chromophore compound into the lens.

SUMMARY OF THE INVENTION

In one embodiment, the present invention is directed to an adjustable chromophore comprising a compound of the formula:

wherein:
i) B is a base chromophore compound; and
ii) X is an adjustable chemical moiety that forms a remaining chemical moiety (C) upon exposure to predetermined electromagnetic radiation thereby forming the compound:

iii) the compound B—C provided greater light absorption than the compound B—X; and
iv) the remaining chemical moiety (C) includes a conjugated double bond.

The present invention is also directed to a lens comprising a polymeric material and the adjustable chromophore compound, as described herein, distributed within the polymeric material. The material that includes the chromophore compound can typically absorb light at progressively greater wavelengths as greater amounts of the compound B—C are formed from the adjustable compound B—X.

The present invention is also directed to a method of adjusting a lens in vivo or in vitro. The method includes directing predetermined electromagnetic radiation as described herein at the above described lens to form the compound B—C either prior to or after implantation of the lens in the eye.

The present invention is also directed to an adjustable chromophore system, comprising a compound of the formula:

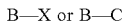

as part of the reactive system:

wherein:
i) B is a base chromophore compound; and
ii) X is an adjustable chemical moiety that forms remaining chemical moiety (C) upon exposure to first predetermined electromagnetic radiation thereby forming the compound B—C:
iii) the compound B—C provides greater light absorption than the compound B—X; and
iv) the remaining chemical moiety (C) includes a conjugated double bond; and
v) optionally, the compound B—C forms the compound B—X upon exposure to second predetermined electromagnetic radiation either with or without the aid of a separable group (S).

The base chromophore of the lens, the system or the adjustable chromophore is preferably selected from the group consisting of benzotriazoles, benzophenones, azo dyes and cinnamate esters. The compound B—C typically absorbs a significant amount of UV light, blue light or both. Moreover, the adjustable chemical moiety X is a preferably a cyclic moiety such as dicyclopentadiene.

DETAILED DESCRIPTION OF THE INVENTION

Figure 1A:
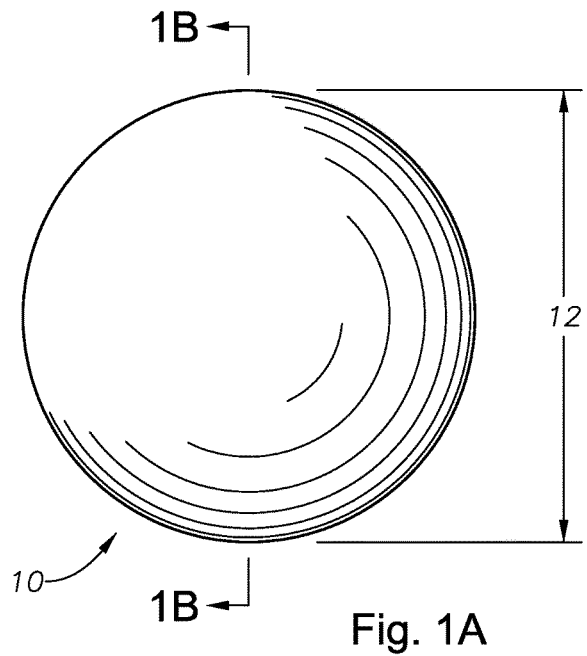
FIGS. 1A and 1B are respectively, a top and sectional view of a contact lens in accordance with an aspect of the present invention.

The present invention is predicated upon the provision of an adjustable chromophore compound and/or system. The absorption characteristics (e.g., absorption profile) of the chromophore compound will be adjustable upon exposure to predetermined electromagnetic radiation. The present invention is also predicated upon the provision of products, particularly lenses (e.g., lens of sunglasses, lenses of spectacles, IOLs, contact lenses or the like), that incorporate the adjustable chromophore compounds and/or system of the present invention such that the absorption profile of those products can be adjusted.

The adjustable chromophore compound will typically have the following chemical structure:

B—X wherein:
B is a base chromophore compound; and
X is an adjustable chemical moiety that forms a separable group (S) and a remaining chemical moiety (C) upon exposure to the predetermined electromagnetic radiation thereby forming the compound:

B—C;

Typically, the remaining chemical moiety (C) includes a conjugated double bond. Advantageously, such conjugated double bond provides significant adjustment to the absorption characteristics (e.g., absorption profile) of resultant chromophore compound B—C relative to the adjustable chromophore compound B—X.

A great number of chromophores are known and may be used as the base chromophore compound (B). In a preferred embodiment, however, the base chromophore compound is selected from the group consisting of benzotriazoles, benzophenones, azo dyes and cinnamate esters. In a highly preferred embodiment the base chromophore compound is a benzotriazole or benzophenone, but is most typically a benzotriazole. Examples of benzotriazoles suitable as the base chromophore compound are disclosed in U.S. Pat. Nos. 4,528,311 and 7,396,942; and U.S. Patent Application Nos. 2010/0012889 and 2008/0090937, all of which are fully incorporated herein in their entirety by reference for all purposes. Other examples of potentially suitable base chromophore compounds are disclosed in US Patent Application Publication Nos. 2007/0077214; 2008/0242818; and 2002/0025401, all of which are fully incorporated herein in their entirety by reference for all purposes.

The adjustable chemical moiety (X) can be any moiety that can be separated into the remaining chemical moiety (C) and the separable group (S) upon exposure to the predetermined electromagnetic radiation. Typically, the chemical moiety (X) is cyclical and, upon separation into the chemical moiety (C) and the separable group (S), provides the chemical moiety (C) with a conjugated double bond. Schematically, such a reaction would be as follows:

Or

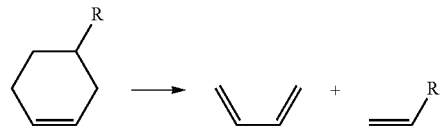

Examples of moieties suitable for use as the adjustable chemical moiety (X) include, without limitation, dicyclopentadiene, dicyclohexadiene, cyclobutane, cyclohexene or the like. It shall be understood that the structures of the chemical moiety (C) and the separable group (S) will be dictated by the structure of the chemical moiety (X) and, in certain circumstance, vice-versa. It will also be understood that the separable group (S) could be bound within a polymer matrix of the polymer, could be entangled in the polymer matrix, but may not be either.

The adjustable chromophore system of the present invention includes an adjustable chromophore compound of the present invention and that adjustable chromophore compound can be adjusted to the resultant chromophore compound B—C but that adjustment is then reversible such that the resultant chromophore compound B—C can be adjusted back to the adjustable compound B—X. Thus, the adjustable chromophore system includes a compound of the formula:

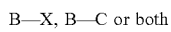

as part of the reactive system:

wherein:
B is the base chromophore compound; and
X is the adjustable chemical moiety that forms separable group (S) and remaining chemical moiety (C) upon exposure to a first predetermined electromagnetic radiation thereby forming the compound B—C where the remaining chemical moiety (C) includes a conjugated double bond. It is then possible that the separation of the adjustable chemical moiety (X) into the remaining chemical moiety (C) and the separable group (S) may be reversible upon exposure to a different predetermined electromagnetic radiation to form the compound B—X. In such instance, the system will be able to add to the level of absorption provided by the system or subtract from the amount of absorption provided by the system depending upon the electromagnetic radiation provided thereto.

The chromophore compound B—X and chromophore compound B—C can include an electron donating chemical moiety (D), an electron withdrawing chemical moiety (W) or both and those moieties will typically remain with the chromophore compound B—C after the adjustable moiety (X) is separated into the remaining moiety (C) and the separable group (S). The donating moiety (D) and the withdrawing moiety (W) can be part of the base chromophore compound (B), the adjustable chemical moiety (X) and/or the remaining chemical moiety (C). Typically, if the donating moiety (D) is part of the base chromophore compound (B), then the withdrawing moiety (W) is part of the adjusting chemical moiety (X) and the remaining chemical moiety (C) and vice versa.

A variety of suitable electron withdrawing moieties (W) will be evident to the skilled artisan. Examples of suitable electron withdrawing moieties (W) include cyano groups, carbonyls, esters, amides, sulfonyls, halogens, combinations thereof or the like. In a preferred embodiment, the withdrawing moiety (W) is a halogen (e.g., a halogen itself or a halogen inclusive group) such as fluorine (F), chlorine (Cl), carbon trifluoride ($CF_3$) or the like. A variety of suitable electron donating moieties (D) will also be evident to the skilled artisan. Examples of suitable donating moieties (D) include, without limitation, alkyl groups such as methyl groups and ethyl groups, alkoxy groups, amino groups or the like.

Advantageously, the donating moiety (D), the withdrawing moiety (W) or both can aid in polarizing the chromophore compound B—C. Such polarization can aid the ability of the chromophore compound B—C in absorbing light, particularly additional wavelengths of light (e.g., higher or longer wavelengths of light). Moreover, such polarization can be significantly blocked by the adjustable chemical moiety (X) such that the light absorption ability of the chromophore compound B—X is significantly reduced (e.g., can be less than 80% or even 60%) relative to the light absorbing ability of the chromophore compound B—C.

The adjustable moiety (X) can additionally or alternatively include a mobilization inhibiting moiety (Z) and that moiety will typically remain with the separable group (S) after the adjustable moiety (X) is separated into the remaining moiety (C) and the separable group (S). Such a mobilization inhibiting moiety (Z) is particularly useful for situation where the chromophore compound B—X is incorporated into a matrix (e.g., a polymer or glass matrix) for maintaining the separable group (S) in the matrix after the adjustable moiety (X) is separated into the remaining moiety (C) and the separable group (S). Typically, the mobilization inhibiting moiety is capable of entangling in the matrix. Preferably, the mobilization inhibiting moiety (Z) is or includes a substituted or unsubstituted alkyl group (e.g., an alkane chain) with a carbon chain or carbon based group having a carbon atoms in the range of $C_4$-$C_{20}$, more typically $C_5$-$C_{12}$ and even possibly $C_6$-$C_{10}$.

The chromophore compounds and/or system of the present invention can be incorporated into a variety of different products. Most significantly, however, they can be incorporated into lenses of products such as sunglasses or spectacles or into contact lenses or IOLs. The chromophore compounds and system can be incorporated into these lenses whether they are formed of glass or polymeric material or a combination thereof. Typically, these materials, whether thermoset or thermoplastic, will form a matrix and the compounds and/or system can be distributed or dispersed throughout the entirety or a portion of the matrix.

The chromophore compounds and/or system of the present invention can be incorporated into matrices of materials commonly used to form sunglasses or spectacles. Such materials can include glass or polymeric materials such as polystyrene, polycarbonate, acrylics, combinations thereof or the like.

The chromophore compounds and/or system of the present invention can be incorporated into contact lenses, IOLs or both. Contact lenses and IOLs typically includes matrices formed of acrylate based materials (i.e., materials that are formed of at least 20%, at least 50% or more acrylate monomers such as phenylethyl methacrylate and hydoxyethyl methacrylate), silicone materials or the like. The skilled artisan will understand that chromophore compounds generally have been included in these types of lenses and/or matrices and the chromophore compounds of the present invention can be incorporated in a similar manner.

The adjustment of the chromophore compound of the present invention can occur prior to incorporation into a product or material matrix, but preferably occurs thereafter. As suggested, the adjustment is caused by exposure of the chromophore compounds, particularly the adjustable moiety (X) to predetermined electromagnetic radiation. The particularly radiation employed to form the adjustable moiety (X) into the remaining moiety (C) and the separable group (S), or vice versa, will depend upon the chemical structure of those groups and/or moieties. That electromagnetic radiation can be from the visible part of the electromagnetic spectrum or from the non-visible part of the electromagnetic spectrum. In preferred embodiments, the predetermined electromagnetic radiation is provided as relatively intense ultraviolet (UV) radiation. In another preferred embodiment, the predetermined radiation is provided as infrared (IR) radiation. In one particularly preferred embodiment, the electromagnetic radiation is provided as two-photon radiation that is typically from the visible portion of the electromagnetic spectrum. Advantageously, the two photon radiation can be provided as light from the visible portion of the electromagnetic spectrum.

The predetermined electromagnetic radiation is provided from a light source such as a laser or other light or energy source that can direct the radiation at the chromophores or at the materials into which the chromophores have been incorporated. Most commonly, the predetermined electromagnetic radiation will have a wavelength and/or frequency configured to result in the following reaction scheme:

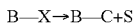

wherein the adjustable chromophore compound B—X is exposed to the predetermined radiation to produce the chromophore compound B—C and the separable group (S). Moreover, within the system of the present invention, a second predetermined electromagnetic radiation will have a wavelength and/or frequency configured to cause the reversal of that reaction.

It will also be understood, particularly with reference to Example 4 below, that the chromophore compound B—X can be converted directly to B—C without the formation of a separable group. This scheme can occur, as it does in Example 4, according to the following reaction scheme:

Alternatively, the chemical entity which would normally be the separable group (S) might be or become chemically bonded with and be part of the base chromophore such that system of the present invention could occur according to the following scheme:

In this invention, the chromophore compound B—C will typically provide a significantly greater amount of light absorption than the adjustable chromophore compound B—X. Moreover, it is possible and often desirable that, as more of the chromophore compound B—C is formed, greater amounts of light at greater wavelengths are absorbed.

In this scenario, the absorption cutoff of the material that include the chromophore compound B—C will move toward progressively higher wavelengths as more and more of the chromophore compound B—C is formed.

As a quantification of this change in absorption, it is desirable for a material including compound B—X to absorb at least 80% of light at a first wavelength and less than 20% of light at a second wavelength when less than 25% of a starting amount or concentration of compound B—X has been converted to compound B—C and separable group (S), but for the material to absorb at least 80% of light at the first wavelength and at least 80% of light at the second wavelength after at least 75% of the starting amount or concentration of the compound B—X has been converted to compound B—C. In such a situation, the first wavelength is at least 5 nanometers, more preferably at least 10 nanometers and even possibly at least 15 nanometers less than the second wavelength.

As suggested above, it is also contemplated that the chromophore compound B—C and separable group (S) can be exposed to predetermined radiation to produce adjustable chromophore compound B—X. As a quantification of this absorption, it is desirable for a material including compound B—C and separable group (S) to absorb at least 80% of light at a first wavelength and light at a second wavelength when less than 25% of a starting amount or concentration of compound B—C and separable group (S) has been converted to compound B—X but for the material to absorb at least 80% of light at the first wavelength but less than 20% of light at the second wavelength after at least 75% of the starting amount or concentration the compound B—C and the separable group (S) has been converted to compound B—X. In such a situation, the first wavelength is at least 5 nanometers, more preferably at least 10 nanometers and even possibly at least 15 nanometers less than the second wavelength.

For ophthalmic lenses, particularly IOLs and/or contact lenses, the chromophores B—X and/or B—C are typically designed to provide substantial absorption (e.g., at least 50% and even at least 80%) of light at wavelengths in the UV range up to and even into portions of the blue light range. As such, the first and second wavelengths, as discussed above, will typically be in the UV to blue portions of the electromagnetic spectrum. Thus, in preferred embodiments, the first and second wavelengths are both preferably in the range of 300 to 500, more preferably 380 to 470 and even more preferably 390 to 440 nanometers.

Figure 1B:
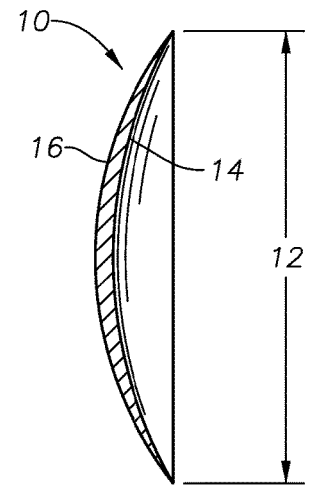
Figure 2A:
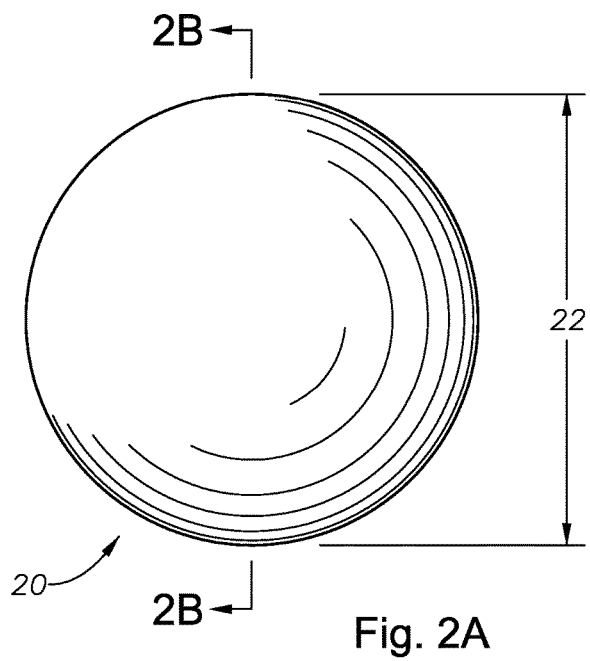
FIGS. 2A and 2B are respectively, a top and sectional view of an intraocular lens in accordance with an aspect of the present invention.
Figure 2B:
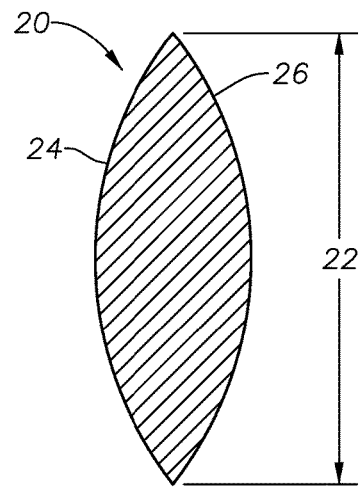

The skilled artisan will understand that the IOLs and contact lenses that will receive the chromophore compounds of the present invention will be sized and shaped suitably for application to the eye. With reference to FIGS. 1A and 1B, a contact lens 10 will typically have a largest outer perimeter (e.g., largest peripheral circumference) 12 of at least 2, more typically at least 3 and even more typically at least 4 centimeters. The largest perimeter 12 will also typically be less than 10, more typically less than 6 and even more typically less than 5.5 centimeters. The contact lens will also typically include a concave surface 14 opposing a convex surface 16. With reference to FIGS. 2A and 2B, an IOL 20 will typically have a largest outer perimeter (e.g., largest peripheral circumference) 22 of at least 1.5, more typically at least 2.0 and even more typically at least 3.2 centimeters. The largest perimeter 22 will also typically be less than 7, more typically less than 5 and even more typically less than 4.5 centimeters. Aphakic IOLs will also typically include a first convex surface 24 opposing a second convex surface 26 whereas phakic IOLs may have convex surfaces like the aphakic IOLs or convex/concave surfaces like the contact lenses.

While these absorption adjustments can occur in vitro, it is also contemplated that they may occur in vivo. For example, and without limitation, both contact lenses and IOLs may be adjusted after application or implantation of those lenses to a mammalian eye, particularly a human eye. This is particularly the case where visible light (e.g., two photon light) is used to adjust the absorption characteristics. A discussion of techniques of using two photon light to adjust refractive index of implanted IOLs is provided in US Patent Publication No. 2009/0157178, which is fully incorporated herein by reference for all purposes. Advantageously, such techniques might also be used to adjust the chromophores of the present invention.

As a further advantage of the present invention, the predetermined radiation can be directed at particular portions of the lens to enhance light absorption in particular pre-selected regions of the lens while other regions of the lens will exhibit less absorption. For an IOL, for example, it might be desirable to enhance the light absorption of a nucleus portion of the IOL while leaving the peripheral portion of the IOL to exhibit less light absorption. Such an IOL would then exhibit the greater light absorption when light is bright and the pupil of the eye is small and would exhibit less absorption when there is less light and the pupil of the eye is larger. In such an embodiment, the nucleus region will typically have a concentration of the chromophore compound B—C that is greater than 120% and more typically greater than 150% of the concentration at a peripheral region of the lens. Such nucleus regions and such peripheral regions will both be at least 10% of the overall volume of the IOL excluding any haptics.

EXAMPLES

Example 1

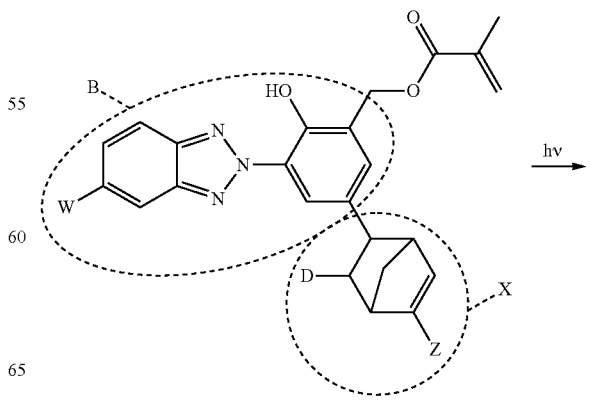

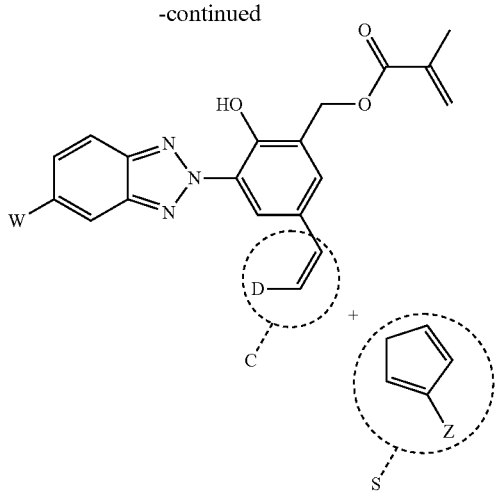

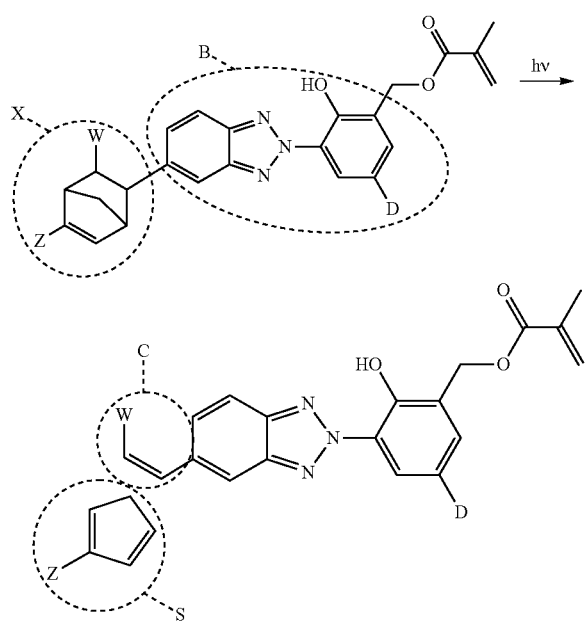

Example 1 above illustrates one exemplary embodiment of the invention. As can be seen, a chromophore compound B—X includes a benzotriazole base chromophore (B) and an adjustable moiety (X), which is a dicyclopentadiene. The adjustable moiety (X) includes a mobilization inhibiting group (Z), which is preferably an alkane chain, and an electron donating moiety (D), which is preferably an alkoxy group. The base chromophore compound (B) includes an electron withdrawing group (W), which is preferably one of the halogen or halogenated groups discussed above. As can be seen, upon exposure to predetermined radiation, the chromophore compound B—X becomes the chromophore compound B—C and separable group (S) with the chromophore compound B—C having a conjugated double bond and the electron donating group (D) as well as the remaining group (C). The base chromophore (B) then includes the electron withdrawing group (W). Further, the separable group (S) includes the mobilization inhibiting group (Z).

Example 2

Example 2 above illustrates another exemplary embodiment of the invention. As can be seen, a chromophore compound B—X includes a benzotriazole base chromophore (B) and an adjustable moiety (X), which is a dicyclopentadiene. The adjustable moiety (X) includes a mobilization inhibiting group (Z), which is preferably an alkane chain, and an electron withdrawing moiety (W), which is preferably a halogen group. The base chromophore compound (B) includes an electron donating group (D), which is preferably an alkoxy group. As can be seen, upon exposure to predetermined radiation, the chromophore compound B—X becomes the chromophore compound B—C and separable group (S) with the chromophore compound B—C having a conjugated double bond and the electron withdrawing group (W) as well as the remaining group (C). The base chromophore (B) then includes the electron donating group (D). Further, the separable group (S) includes the mobilization inhibiting group (Z).

Example 3

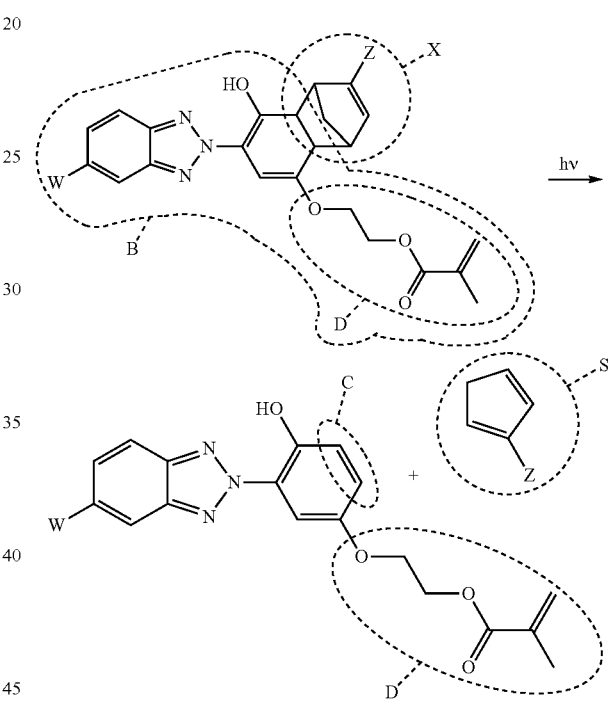

Example 3 above illustrates another exemplary embodiment of the invention. As can be seen, a chromophore compound B—X includes a benzotriazole base chromophore (B) and an adjustable moiety (X), which is a dicyclopentadiene. In this example, a cyclic moiety of the base chromophore (B) and the dicyclopentadiene share a common bond. The adjustable moiety (X) includes a mobilization inhibiting group (Z), which is preferably an alkane chain. Further, the w base chromophore (B) includes an electron withdrawing moiety (W), which is preferably a halogen group and an electron donating group (D), which preferably includes an alkoxy group. As can be seen, upon exposure to predetermined radiation, the chromophore compound B—X become the chromophore compound B—C and separable group (S) with the chromophore compound B—C having a is conjugated double bond as the remaining group (C) and the electron withdrawing group (W). The base chromophore (B) also includes the electron donating group (D). Further, the separable group (S) includes the mobilization inhibiting group (Z), Example 4

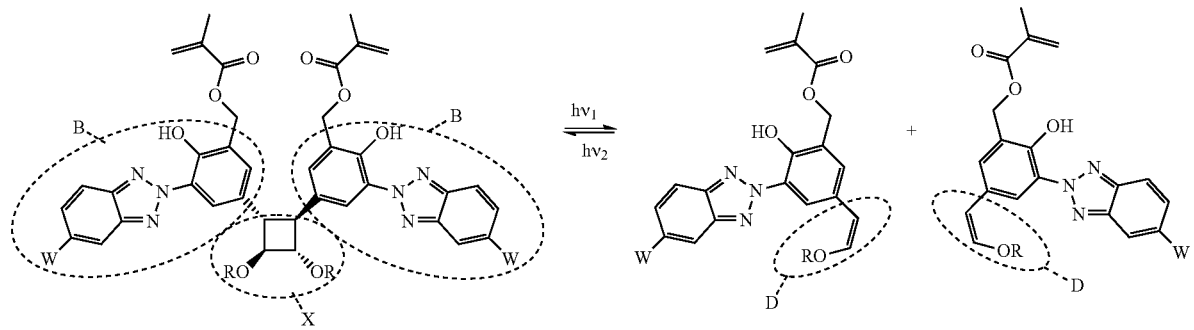

Example 4 above illustrates another exemplary embodiment of the system of the invention. As can be seen, a pair of base chromophore compounds (B), which are both benzotriazoles are both bonded to a single adjustable moiety (X), which is a cyclobutane, to form the compound B—X—B. Each of the base chromophore compounds (B) include both an electron withdrawing moiety (W), which is preferably a halogen group and an electron donating group (D), which preferably includes an alkoxy group. As can be seen, upon exposure to predetermined radiation, the chromophore compound B—X—B becomes two separate chromophore compounds B—C with each of the chromophore compounds B—C having a remaining group (C) with a conjugated double bond. Moreover, upon exposure to a second predetermined radiation, the chromophore compounds B—C can be reacted to become the single chromophore compound B—X—B.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

I claim:

1. A method of adjusting the light absorption characteristics of an intraocular lens, the method comprising:
   implanting into a patient a lens having a compound selected from the group consisting of:

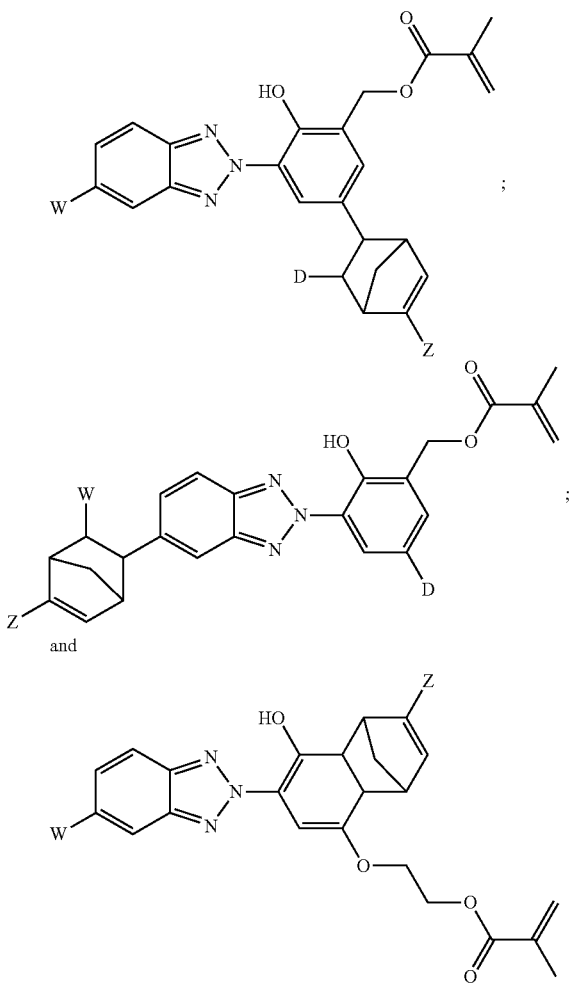

wherein W is an electron withdrawing moiety;
   D is an electron donating moiety; and
   Z is a mobilization inhibiting moiety; and
   exposing the lens to electromagnetic radiation sufficient to adjust the amount of UV light, blue light, or both that the lens absorbs.

2. The method of claim 1 wherein W is selected from the group consisting of Cl, F, and $CF_3$.

3. The method of claim 1 wherein D is selected from the group consisting of alkyl, alkoxy, and amino groups.

4. The method of claim 1 wherein Z is selected from the group consisting of unsubstituted or substituted $C_4$-$C_{20}$ alkyl.

* * * * *